United States Patent
Zhang et al.

(10) Patent No.: US 12,379,202 B2
(45) Date of Patent: Aug. 5, 2025

(54) METHOD FOR PREDICTING VAULT AFTER PHAKIC INTRAOCULAR LENS AND ELECTRONIC DEVICE

(71) Applicant: Hangzhou MSK Eye Hospital Co.LTD, Hangzhou (CN)

(72) Inventors: Jun Zhang, Hangzhou (CN); Li Zheng, Hangzhou (CN)

(73) Assignee: Hangzhou MSK Eye Hospital Co.LTD, Hangzhou (CN)

( * ) Notice: Subject to any disclaimer, the term of this patent is extended or adjusted under 35 U.S.C. 154(b) by 304 days.

(21) Appl. No.: 17/954,621

(22) Filed: Sep. 28, 2022

(65) Prior Publication Data

US 2023/0142276 A1    May 11, 2023

(51) Int. Cl.
    G01B 11/06    (2006.01)
(52) U.S. Cl.
    CPC .......... *G01B 11/06* (2013.01); *G01B 11/0608* (2013.01)
(58) Field of Classification Search
    CPC .............................. G01B 11/06; G01B 11/0608
    See application file for complete search history.

(56) References Cited

FOREIGN PATENT DOCUMENTS

| CN | 101827565 A | * 9/2010 | .......... A61F 2/1602 |
|----|-------------|----------|-----------------------|
| CN | 205831963 U | * 12/2016 | |
| CN | 114742008 A | 7/2022 | |
| CN | 114767330 A | 7/2022 | |

OTHER PUBLICATIONS

Jaeryung "Direct Measurement of the Ciliary Sulcus Diameter by 35-Megahertz Ultrasound Biomicroscopy", pp. 1685-1688, Aug. 22, 2006 (Year: 2006).*
"Correlation between ciliary sulcus diameter measured by 35 MHz ultrasound biomicroscopy and other ocular measurements" Kyun-Hyung Kim et.al., pp. 632-637 (Year: 2008).*
"Evaluation of ciliary sulcus diameter using ultrasound biomicroscopy in emmetropic eyes and myopic eyes" Julia Biermann, MD, Laura Bredow, MD, et al., pp. 1686-1693 (Year: 2011).*

* cited by examiner

*Primary Examiner* — Michael J Dalbo
*Assistant Examiner* — Kaleria Knox
(74) *Attorney, Agent, or Firm* — Getech Law LLC; Jun Ye

(57) ABSTRACT

Provided are a method for predicting a Vault after phakic intraocular lens and an electronic device. After a thickness of a to-be-corrected crystalline lens, and a horizontal sulcus-to-sulcus value and a vertical sulcus-to-sulcus value corresponding to the to-be-corrected crystalline lens are obtained, a diameter ICL Size and an axial position ICL Ax of a preset ICL lens are collected, an effective sulcus-to-sulcus value, a lens thickness influence factor LTF, a Vault chord height h and the Vault are sequentially calculated according to the obtained data, and whether the diameter ICL Size and the axial position ICL Ax of the currently adopted ICL lens meet the Vault requirement or not is judged according to the Vault. The predicting accuracy and precision of a lens position after ICL lens implantation is reduced, postoperative complications are reduced, and the convenience of clinical operation and the safety of ICL operation are improved.

6 Claims, 3 Drawing Sheets

METHOD FOR PREDICTING VAULT AFTER PHAKIC INTRAOCULAR LENS AND ELECTRONIC DEVICE

CROSS REFERENCE TO RELATED APPLICATIONS

This application claims foreign priority of Chinese Patent Application No. 202111324593.3, filed on Nov. 10, 2021 in the China National Intellectual Property Administration, the disclosures of all of which are hereby incorporated by reference.

TECHNICAL FIELD

The present invention belongs to the field of intraocular lenses and correction of refractive errors, and particularly relates to a method for predicting a Vault after phakic intraocular lens, a method for determining a lens size of phakic intraocular lens and an electronic device.

BACKGROUND

Posterior chamber phakic intraocular lens is an intraocular lens implantation operation of an implantable collamer lens (ICL) in a posterior chamber, which may effectively and safely correct various refractive errors. When correction of refractive errors is carried out by the method above, a distance between a rear surface of the ICL and a front surface of a natural lens is called a Vault, which is closely related to postoperative complications, and is a key parameter to determine whether the operation is successful. An insufficient Vault (<90 µm) may increase a formation risk of cataract, while a too high Vault (>1,000 µm) may lead to closure of an anterior chamber angle (ACA), pigment diffusion, pupillary block or endothelial cell injury. Selecting an appropriate ICL size and reaching a safety level of a vault are main factors to avoid complications after ICL implantation.

In the prior art, there are still problems such as the too high or insufficient Vault after operation, the Vault may be adjusted by a secondary operation, and a proportion of secondary operation by ICL rotation or ICL replacement for Vault adjustment is about 0.8%. However, the secondary operation can increase a physical burden of a patient by several times, and a difficulty coefficient of the ICL replacement is increased, so that it is difficult to replace the ICL, thus increasing an operation risk.

SUMMARY

In order to solve the problems that a Vault of posterior chamber phakic ICL in the prior art is too high or insufficient, an embodiment of the present invention provides a method for predicting a Vault after phakic intraocular lens ZZ ICL Vault Formula, a method for determining a lens size of phakic intraocular lens and an electronic device, which improve the predicting accuracy and precision of a lens position after ICL lens implantation, reduce postoperative complications, and meanwhile, improve the convenience of clinical operation and improve the safety of ICL operation.

In order to achieve the above object, the following technical solutions are used in the embodiment of the present invention.

In a first aspect, the embodiment of the present invention provides a method for predicting a Vault after phakic intraocular lens, which comprises the following steps of:

step S1: obtaining a thickness LT of a to-be-corrected crystalline lens;

step S2: obtaining a horizontal sulcus-to-sulcus STSH value and a vertical sulcus-to-sulcus STSV value corresponding to the to-be-corrected crystalline lens;

step S3: collecting a size of a preset ICL lens, comprising a diameter ICL Size and an axial position ICL Ax of the ICL lens;

step S4: calculating an effective sulcus-to-sulcus STS value at the axial position of the ICL lens by formulas (1) and (2) according to the STSH and the STSV:

when ICL Ax≤90, $$STS=STSH-(STSH-STSV)\times\sin \text{ICL } Ax\times1586.5\div1555 \quad (1);$$

and
when ICL Ax>90, $$STS=STSH-(STSH-STSV)\times\sin(180-\text{ICL } Ax)\times1586.5\div1555 \quad (2);$$

step S5: calculating a lens thickness influence factor LTF by formula (3) according to the LT:

$$LTF=LT\div10+0.16 \quad (3);$$

step S6: calculating a Vault chord height h by formula (4) according to the ICL Size and the STS:

$$h=(\text{ICL Size}-STS)^{0.7} \quad (4);$$

step S7: calculating the Vault by formula (5) according to the h and the LTF:

$$\text{Vault}=h-LTF \quad (5);$$

and
step S8: judging whether the Vault reaches a threshold: when the Vault does not reach the threshold, updating the diameter ICL Size and the axial position ICL Ax of the ICL lens, and entering the step S4.

In the above solution, the STSH and the STSV are obtained by an ultrasonic biomicroscope UBM or a biometer.

In the above solution, the size of the preset ICL lens is selected according to at least one of experience and STSH, STSV and LT data.

In the above solution, the threshold is a point value or a range.

In the above solution, the threshold ranges from 0.5 to 1.0; and when the Vault falls within the range of the threshold, the Vault reaches the threshold.

In a second aspect, the embodiment of the present invention further provides a method for determining a lens size of phakic intraocular lens, which comprises: step S1: obtaining a thickness LT of a to-be-corrected crystalline lens;

step S2: obtaining a horizontal sulcus-to-sulcus STSH value and a vertical sulcus-to-sulcus STSV value corresponding to the to-be-corrected crystalline lens;

step S3: collecting a size of a preset ICL lens, comprising a diameter ICL Size and an axial position ICL Ax of the ICL lens;

step S4: calculating an effective sulcus-to-sulcus STS value at the axial position of the ICL lens by formulas (1) and (2) according to the STSH and the STSV:

when ICL Ax≤90, $$STS=STSH-(STSH-STSV)\times\sin \text{ICL } Ax\times1586.5\div1555 \quad (1);$$

and
when ICL Ax>90, $$STS=STSH-(STSH-STSV)\times\sin(180-ICL\ Ax)\times 1586.5\div1555 \quad (2);$$

step S5: calculating a lens thickness influence factor LTF by formula (3) according to the LT:

$$LTF=LT\div10+0.16 \quad (3);$$

step S6: calculating a Vault chord height h by formula (4) according to the ICL Size and the STS:

$$h=(ICL\ Size-STS)^{0.7} \quad (4);$$

step S7: calculating the Vault by formula (5) according to the h and the LTF:

$$Vault=h-LTF \quad (5);$$

and step S8: judging whether the Vault reaches a threshold: when the Vault does not reach the threshold, updating the diameter ICL Size and the axial position ICL Ax of the ICL lens, and entering the step S4.

In a third aspect, the embodiment of the present invention further provides an electronic device, which comprises a processor, a memory and a human-computer interaction module; and data transmission is carried out among the processor, the memory and the human-computer interaction module, wherein:

the human-computer interaction module is configured for inputting collected data and sending the collected data to the processor;

the memory is configured for storing a computer program and related data; and the processor is configured for receiving the data input by the human-computer interaction module, and executing the program stored in the memory; and when receiving the data input by the human-computer interaction module, implementing the following steps of:

step S1: obtaining a thickness LT of a to-be-corrected crystalline lens;

step S2: obtaining a horizontal sulcus-to-sulcus (STSH) value and a vertical sulcus-to-sulcus (STSV) value corresponding to the to-be-corrected crystalline lens;

step S3: collecting a size of a preset ICL lens, comprising a diameter ICL Size and an axial position ICL Ax of the ICL lens;

when executing the program stored in the memory, implementing the following steps of:

step S4: calculating an effective sulcus-to-sulcus STS value at the axial position of the ICL lens by formulas (1) and (2) according to the STSH and the STSV:

when ICL Ax≤90, $$STS=STSH-(STSH-STSV)\times\sin ICL\ Ax\times1586.5\div1555 \quad (1);$$

and when ICL Ax>90, $$STS=STSH-(STSH-STSV)\times\sin(180-ICL\ Ax)\times 1586.5\div1555 \quad (2);$$

wherein in the step, formula parameters are determined through a lot of experiments and theoretical derivation;

step S5: calculating a lens thickness influence factor LTF by formula (3) according to the LT:

$$LTF=LT\div10+0.16 \quad (3);$$

step S6: calculating a Vault chord height h by formula (4) according to the ICL Size and the STS:

$$h=(ICL\ Size-STS)^{0.7} \quad (4);$$

step S7: calculating the Vault by formula (5) according to the h and the LTF:

$$Vault=h-LTF \quad (5);$$

and step S8: judging whether the Vault reaches a threshold: when the Vault does not reach the threshold, updating the diameter ICL Size and the axial position ICL Ax of the ICL lens, and entering the step S4.

The method for predicting the Vault after phakic intraocular lens ZZ ICL Vault Formula provided by the embodiment of the present invention has the following beneficial effects:

according to the method for predicting the Vault after phakic intraocular lens and the electronic device in the embodiment of the present invention, traditional white-to-white estimation is bypassed, and deformation of the ICL lens is directly calculated through sulcus-to-sulcus data, so as to predict the Vault after operation; disadvantages of a previous statistical regression algorithm are abandoned, and a possible influence of individual difference can be significantly reduced; the Vault is quantitatively predicted, the predicting accuracy and precision of the Vault are improved, a personalized operation design is conveniently carried out clinically, a long-term safety of operation is improved, an operating procedure is optimized, and a clinical effect is improved; and meanwhile, the method and the electronic device may also be used to determine the lens size of ICL implantation, so that the accuracy and safety of the personalized operation design are improved.

Certainly, it is not necessary to achieve all the advantages mentioned above at the same time to implement any product or method of the present invention.

BRIEF DESCRIPTION OF THE DRAWINGS

In order to illustrate the technical solutions in the embodiments of the present invention more clearly, the drawings used in the descriptions of the embodiments will be briefly introduced below. Obviously, the drawings in the following descriptions are merely some embodiments of the present invention. For those of ordinary skills in the art, other drawings may also be obtained based on these drawings without going through any creative work.

DETAILED DESCRIPTION

Figure 1:
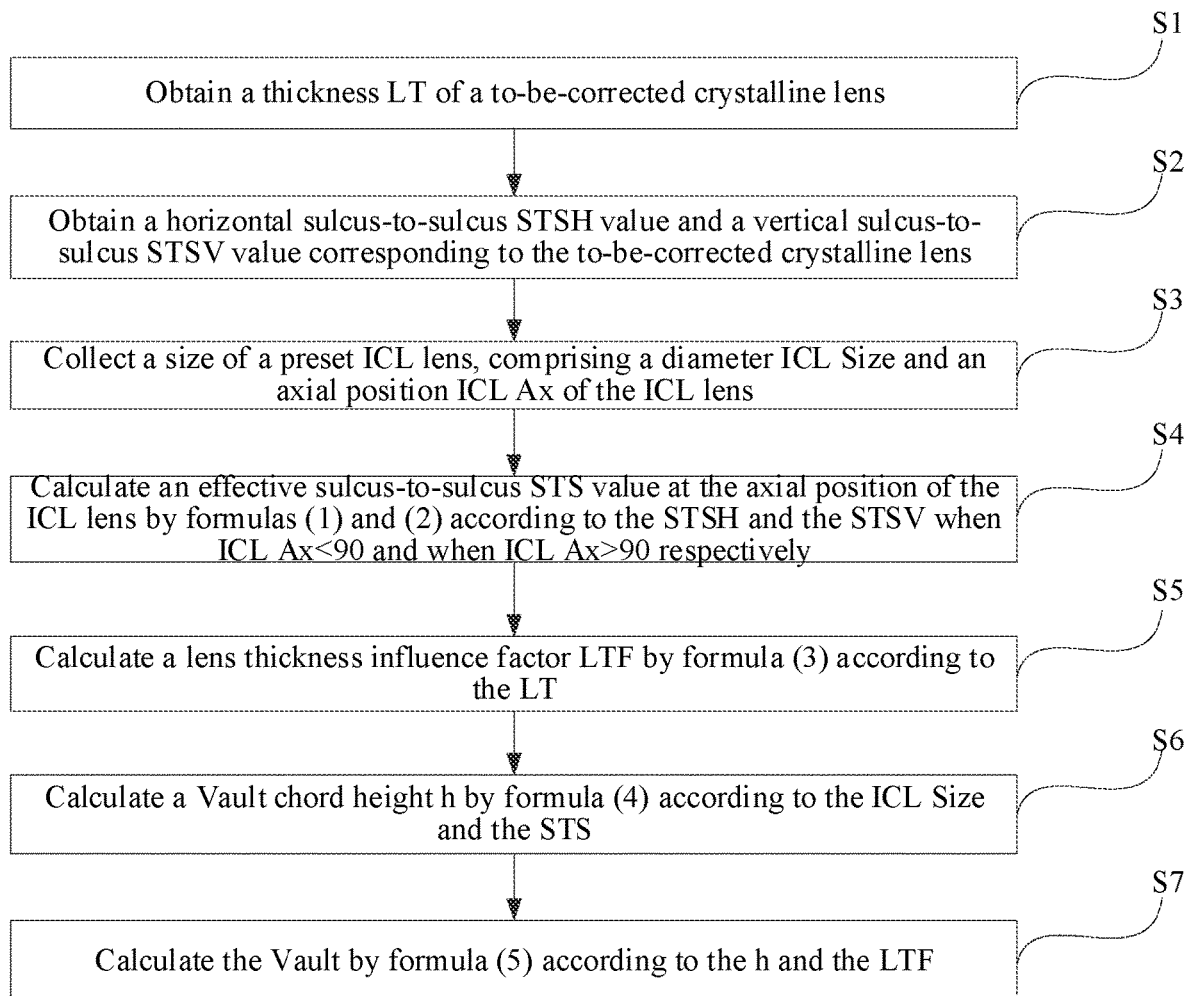
FIG. 1 is a flow chart of a method for predicting a Vault after phakic intraocular lens in an embodiment of the present invention.

The inventor of the present application made an in-depth study on the problems that a Vault of posterior chamber phakic ICL in the prior art was too high or insufficient with a view to reducing probabilities of the problems by improving the predicting accuracy of the Vault after operation.

After the in-depth study, the inventor of the present application found that a currently used method for determining a size of an ICL was generally based on an on-line calculator and an ordering system recommended and provided by manufacturers, such as a STAAR system. This method was based on a horizontal corneal white-to-white (WTW) distance and an anterior chamber depth (ACD), but a clinical feedback was not ideal, and about 20% of cases exceeded an acceptable Vault range (<250 μm and >1,000 μm). Another method for determine the size of the ICL was based on sulcus-to-sulcus (STS) diameter measurement by an ultrasonic biomicroscope (UBM). However, the above two measurement methods comprising the WTW method and the STS method still have the following problems: firstly, the ICL is designed to be placed according to a STS diameter, and a correlation between the STS diameter and a WTW diameter has been proved to be poor; secondly, STS measurement is very important and subjective, but there is a lack of detailed operation instruction at present; thirdly, there is a problem in a selection standard of a measurement image of "four bright reflection bands" suggested by a UBM manufacturer, which may lead to more important selection deviation, and there is no relevant discussion and analysis literature in the world at present; due to an image acquisition principle of the UBM, the image of "four bright reflection bands" refers to that central bands of front and rear surfaces of the cornea and the lens are perpendicular to a probe, but a STS in this image has no correlation with a maximum STS in the same direction clinically, and the maximum STS in the same direction is an effective STS position after ICL implantation theoretically; fourthly, when only the Vault is directly predicted only by the STS and the ICL/TICL size, an influence of a natural lens coefficient is ignored and should be compensated; and fifthly, a natural position of an original lens may move after ICL implantation.

In view of the defects of the above methods for measuring the ICL size, there are the following problems in Vault prediction: an indirect method of spatial prediction for lens implantation has a poor correlation, a low predicting accuracy and unsatisfactory clinical results; direct measurement of a lens implantation space may be realized by the UBM, but a detection device is greatly influenced by a subjective factor of an operator, and there is a lack of a standardized operation method, so that the previous measurement method fails to get better clinical results; from the technical level, an intraocular lens with a larger diameter should be placed in a limited space, and a related influence of the natural lens should also be considered at the same time, which is mainly done by a statistical regression formula at present, but the formula is imperfect in consideration, and the individual difference has a significant influence on results, so that a universality is poor; all relevant methods in the world are still qualitative evaluation at present, and there is no quantitative evaluation; and meanwhile, the method for predicting the Vault is not convenient enough, which is not conducive to operation.

It should be noted that the above defects of the solutions in the prior art are all results of the inventor obtained through practice and careful study. Therefore, the discovery process of the above problems and the solutions proposed by the embodiments of the present invention below for the above problems should be the contributions made by the inventor to the present invention during the process of the present invention.

The technical solutions in the embodiments of the present invention are clearly and completely described hereinafter with reference to the drawings in the embodiments of the present invention. Obviously, the embodiments described are merely a part of, rather than all of, the embodiments in the present invention. Generally, the assemblies in the embodiments of the present invention described and illustrated in the drawings herein may be arranged and designed in various different configurations. It should be noted that, in the case of no conflict, the embodiments in the present invention and the features in the embodiments may be combined with each other.

It should be noted that: similar reference numerals and letters indicate similar items in the following drawings, so once one item is defined in one drawing, it does not need to be further defined and explained in the following drawings. In the description of the present invention, the terms "first", "second", "third", "fourth", and the like are used to distinguish the descriptions only and cannot be understood as indicating or implying relative importance.

After the above-mentioned in-depth analysis, the inventor of the present application proposed a method for predicting a Vault after phakic intraocular lens, which is called a ZZ ICL Vault Formula method, and an electronic device, based on cognition of anatomical relative position and change after phakic intraocular lens and cognition of regulation after conversion of compression deformation into a digital model in combination with theories of physics and applied mathematics, which improved predicting accuracy and precision of a lens position after ICL lens implantation, reduced postoperative complications, and meanwhile, improved the convenience of clinical operation and improved the safety of ICL operation, and facilitated a refractive surgeon to simply improve a clinical effect of ICL lens implantation according to relevant standardized operation procedures on the premise of ensuring safety.

With reference to FIG. 1, an embodiment of the present invention provides a method for predicting a Vault after phakic intraocular lens, which comprises the following steps.

In step S1, a thickness LT of a to-be-corrected crystalline lens is obtained.

In the step, the thickness of the to-be-corrected crystalline lens may be inspected by a biometer.

In step S2, a horizontal sulcus-to-sulcus STSH value and a vertical sulcus-to-sulcus STSV value corresponding to the to-be-corrected crystalline lens are obtained.

In the step, the STSH and the STSV are eye data of a patient with the to-be-corrected crystalline lens, and may be inspected by an ultrasonic biomicroscope UBM or the biometer. The STSH and the STSV herein are both effective values. When the inspection is not carried out by the ultrasonic biomicroscope UBM or the biometer, measurement results are effective values on the premise that an inspected image is clear. When the inspected image is blurred and a measurement boundary is not clear, the measurement results are ineffective and unusable. The definition of being clear may be judged by a device, or judged manually according to attempt errors, and the ineffective values are deleted.

The sulcus-to-sulcus refers to ciliary sulcus to ciliary sulcus, which is anatomically normal eye data. In the step, when a sulcus-to-sulcus distance of a ciliary body is measured according inspection data of the UBM, an eye axis is measured by a sound velocity, and in order to avoid or reduce theoretical deviation, calculation of the sound velocity should be revised to further improve predicting accuracy and precision of the Vault.

In step S3, a size of a preset ICL lens is obtained, comprising a diameter ICL Size and an axial position ICL Ax of the ICL lens.

In the step, the size of the preset ICL lens may be preliminarily judged and then selected according to at least one of experience, a type of ICL, and STSH, STSV and LT data and other eye data of a patient. For example, the ICL Size is selected according to four models of ICL and guidance values of a manufacture, wherein the four models comprise 12.1; 12.6; 13.2; and 13.7; and the ICL Ax usually starts from 0.

In the step, the size of the preset ICL lens may also be adjusted according to a predicted Vault value, and the Vault value is predicted again after adjustment, until the Vault value satisfies an expectation. For example, a threshold is set, whether the Vault obtained in step S7 reaches the threshold is judged; and when the Vault does not reach the threshold, the diameter ICL Size and the axial position ICL Ax of the ICL lens are updated. The threshold may be set according to clinical expectations or actual needs, and may be a point value or a range, such as ranging from 0.5 to 1.0. When the threshold is set to be one range, the Vault reaches the threshold when falling within the range of the threshold. The updating of the diameter ICL Size and the axial position ICL Ax of the ICL lens may be changed and selected based on the size of the preset ICL lens according to a difference between the Vault and the threshold.

In step S4, an effective sulcus-to-sulcus STS value at the axial position of the ICL lens is calculated by formulas (1) and (2) according to the STSH and the STSV:

when ICL Ax≤90, $$STS=STSH-(STSH-STSV)\times\sin \text{ICL } Ax\times1586.5\div1555 \quad (1);$$

and when ICL Ax>90, $$STS=STSH-(STSH-STSV)\times\sin(180-\text{ICL } Ax)\times1586.5\div1555 \quad (2);$$

In the step, formula parameters are determined through a lot of experiments and theoretical derivation.

In step S5, a lens thickness influence factor LTF is calculated by formula (3) according to the LT:

$$LTF=LT\div10+0.16 \quad (3);$$

In step S6, a Vault chord height h is calculated by formula (4) according to the ICL Size and the STS:

$$h=(\text{ICL Size}-STS)^{0.7} \quad (4);$$

In step S7, the Vault is calculated by formula (5) according to the h and the LTF:

$$\text{Vault}=h-LTF \quad (5);$$

Figure 2:
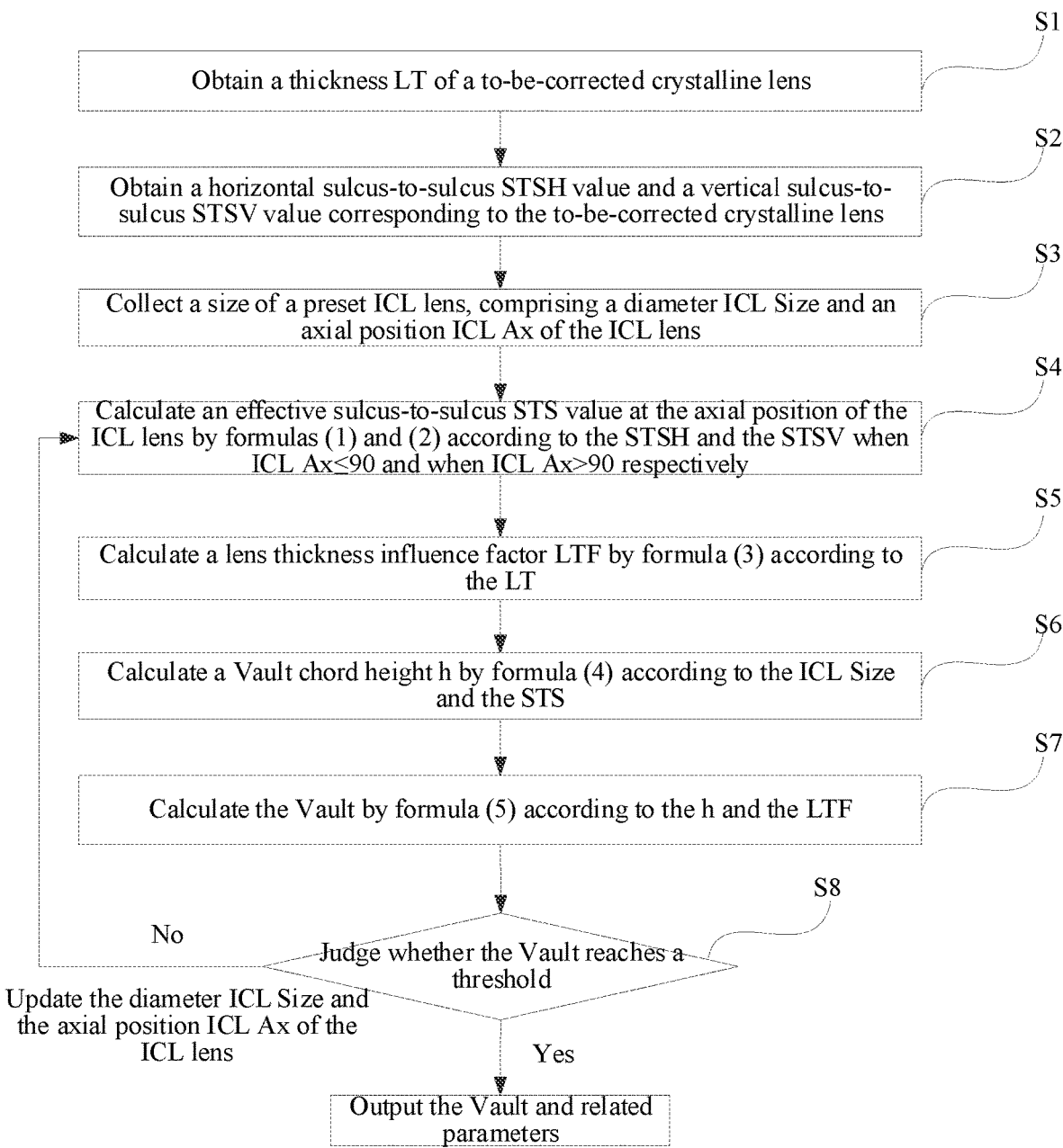
FIG. 2 is a flow chart of a method for determining a lens size of phakic intraocular lens in an embodiment of the present invention.

Based on the method for predicting the Vault above, the embodiment of the present invention further provides a method for determining a lens size of phakic intraocular lens. As shown in FIG. 2, the method for determining the lens size comprises:

step S1: obtaining a thickness LT of a to-be-corrected crystalline lens;

step S2: obtaining a horizontal sulcus-to-sulcus STSH value and a vertical sulcus-to-sulcus STSV value corresponding to the to-be-corrected crystalline lens;

step S3: collecting a size of a preset ICL lens, comprising a diameter ICL Size and an axial position ICL Ax of the ICL lens;

step S4: calculating an effective sulcus-to-sulcus STS value at the axial position of the ICL lens by formulas (1) and (2) according to the STSH and the STSV:

when ICL Ax≤90, $$STS=STSH-(STSH-STSV)\times\sin \text{ICL } Ax\times1586.5\div1555 \quad (1);$$

and when ICL Ax>90, $$STS=STSH-(STSH-STSV)\times\sin(180-\text{ICL } Ax)\times1586.5\div1555 \quad (2);$$

step S5: calculating a lens thickness influence factor LTF by formula (3) according to the LT:

$$LTF=LT\div10+0.16 \quad (3);$$

step S6: calculating a Vault chord height h by formula (4) according to the ICL Size and the STS:

$$h=(\text{ICL Size}-STS)^{0.7} \quad (4);$$

step S7: calculating the Vault by formula (5) according to the h and the LTF:

$$\text{Vault}=h-LTF \quad (5);$$

and step S8: judging whether the Vault reaches a threshold: when the Vault does not reach the threshold, updating the diameter ICL Size and the axial position ICL Ax of the ICL lens, and entering the step S4.

In the step, the threshold may be set according to clinical expectations or actual needs, and may be a point value or a range, such as ranging from 0.5 to 1.0. When the threshold is set to be one range, the Vault reaches the threshold when falling within the range of the threshold. The updating of the diameter ICL Size and the axial position ICL Ax of the ICL lens may be changed and selected based on the size of the preset ICL lens according to a difference between the Vault and the threshold.

The embodiment of the present invention is further described in detail hereinafter through a specific application example.

Before phakic intraocular lens of a patient needing eye refractive correction, a thickness LT of a to-be-corrected lens is collected by a biometer, LT=3.61; then, effective horizontal sulcus-to-sulcus STSH and vertical sulcus-to-sulcus STSV values of an eye of the patient are collected by an ultrasonic biomicroscope UBM, wherein STSH=11.65 and STSV=12.07.

According to experience and corresponding eye data, a size of a preset ICL lens is that ICL Size=13.2 and ICL Ax=0.

An effective STS at an axial position of an effective ICL lens is calculated by formula (1):

when ICL Ax≤90, $$STS=STSH-(STSH-STSV)\times\sin \text{ICL } Ax\times1586.5\div1555;$$

A lens thickness influence factor LTF is calculated by formula (3):

$$LTF=LT\div10+0.16;$$

A Vault chord height h is calculated by formula (4):

$$h=(\text{ICL Size}-STS)^{0.7}$$

The Vault is calculated by formula (5):

$$\text{Vault}=h-LTF;$$

A clinically expected Vault of the patient is between 0.50 and 1.00, so that 0.69 reaches the threshold, which meets a clinical requirement. That is, when an ICL lens with a size of 13.2 is implanted and placed at an axial position of horizontal 0, the Vault after operation is predicted to be 0.69, which may realize safe and effective phakic intraocular lens to perform refractive correction for the patient. Through clinical observation, an actual Vault of the patient is 0.69 after phakic intraocular lens with the above parameters, which effectively improves predicting accuracy and precision of the Vault.

When a traditional method is used, an ICL lens with a size of 12.6 should be implanted according to a white-to-white value (WTW=11.2), and the Vault after operation may only be 0.27, which fails to fall within an expected range of operation, and can increase an occurrence rate of postoperative complications.

It can be seen from the above technical solutions that, according to the method for predicting the Vault after phakic intraocular lens, which is the ZZ ICL Vault Formula method, and the electronic device provided by the embodiment of the present invention, traditional white-to-white estimation is bypassed, and deformation of the ICL lens is directly calculated through sulcus-to-sulcus data, so as to predict the Vault after operation; disadvantages of a previous statistical regression algorithm are abandoned, and a possible influence of individual difference can be significantly reduced; and the Vault is quantitatively predicted, the predicting accuracy and precision of the Vault are improved, a personalized operation design is conveniently carried out clinically, a long-term safety of operation is improved, an operating procedure is optimized, and a clinical effect is improved. For example, when the size of the ICL lens is adjusted, an increase or decrease amount of the Vault is quantitatively estimated, or a change result of the Vault when the lens expands many years later is speculated.

Figure 3:
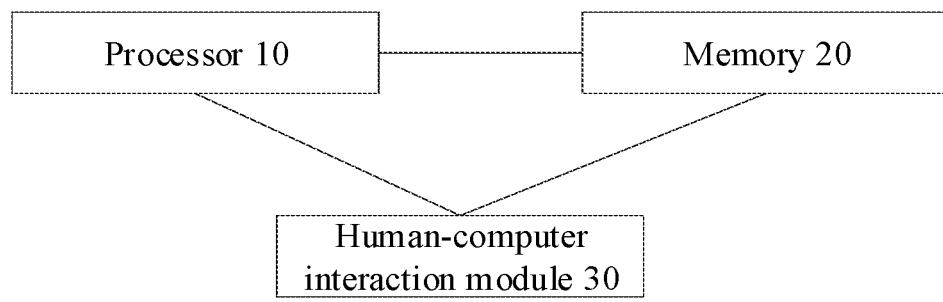
FIG. 3 is a schematic structural diagram of an electronic device provided by an embodiment of the present invention.

Based on the same idea, the embodiment of the present invention further provides an electronic device, and as shown in FIG. 3, the device comprises a processor 10, a memory 20 and a human-computer interaction module 30. Data transmission may be carried out among the processor 10, the memory 20 and the human-computer interaction module 30.

The human-computer interaction module 30 is configured for inputting collected data and sending the collected data to the processor.

The memory 20 is configured for storing a computer program and related data.

The processor 10 is configured for receiving the data input by the human-computer interaction module 30, and executing the program stored in the memory 20; and when receiving the data input by the human-computer interaction module 30, implementing the following steps.

In step S1, a thickness LT of a to-be-corrected crystalline lens is obtained.

In step S2, a horizontal sulcus-to-sulcus (STSH) value and a vertical sulcus-to-sulcus (STSV) value corresponding to the to-be-corrected crystalline lens are obtained In step S3, a size of a preset ICL lens is collected, comprising a diameter ICL Size and an axial position ICL Ax of the ICL lens.

When the program stored in the memory 20 is executed, the following steps are implemented.

In step S4, an effective sulcus-to-sulcus STS value at the axial position of the ICL lens is calculated by formulas (1) and (2) according to the STSH and the STSV:

when ICL Ax≤90, $$STS = STSH - (STSH - STSV) \times \sin ICL\ Ax \times 1586.5 \div 1555 \qquad (1);$$

and
when ICL Ax>90, $$STS = STSH - (STSH - STSV) \times \sin(180 - ICL\ Ax) \times 1586.5 \div 1555 \qquad (2);$$

In the step, formula parameters are determined through a lot of experiments and theoretical derivation.

In step S5, a lens thickness influence factor LTF is calculated by formula (3) according to the LT:

$$LTF = LT \div 10 + 0.16 \qquad (3);$$

In step S6, a Vault chord height h is calculated by formula (4) according to the ICL Size and the STS:

$$h = (ICL\ Size - STS)^{0.7} \qquad (4);$$

In step S7, the Vault is calculated by formula (5) according to the h and the LTF:

$$Vault = h - LTF \qquad (5);$$

When the program stored in the memory 20 is executed by the processor 10, the following steps may also be implemented.

In step S8, whether the Vault reaches a threshold is judged: when the Vault does not reach the threshold, the diameter ICL Size and the axial position ICL Ax of the ICL lens are updated, and the step S4 is entered.

The human-computer interaction module may be realized by image devices such as a touch display.

The memory may include a RAM (Random Access Memory), and may also include a Non-Volatile memory (NVM), such as at least one disk memory. Optionally, the memory may also be at least one storage device disposed far from the forgoing processor.

The processor may be a microprocessor MPU, a Central Processing Unit (CPU), a Network Processor (NP) or a Digital Signal Processor (DSP), an Application Specific Integrated Circuit (ASIC), a Field Programmable Gate Array (FPGA), or other programmable logic device, discrete gate or transistor logic device, discrete hardware assembly, etc.

Data transmission among various modules of the above electronic device may be realized by an interconnection method or a data bus. The data bus may be a peripheral component interconnect (PCI) bus or an extended industry standard architecture (EISA) bus, and may be divided into an address bus, a data bus and a control bus.

In the above-mentioned embodiments, it may be realized in whole or in part by software, hardware, firmware or any combination thereof. When it is implemented using software, it may be implemented in whole or in part in the form of a computer program product. The computer program product includes one or more computer instructions. When the computer program instructions are loaded and executed on a computer, the processes or functions according to the embodiments of the present invention are generated in whole or in part. The computer may be a general purpose computer, a special purpose computer, a computer network, or other programmable apparatus. The computer instruction may be stored in a computer-readable storage medium or transmitted from one computer-readable storage medium to another computer-readable storage medium, for example, the computer instruction may be transmitted from one website site, computer, server or data center to another web site, computer, server or data center by wired (e.g., coaxial cable, optical fiber, Digital Subscriber Line (DSL)) or wireless (e.g., infrared, wireless, microwave, etc.) manners. The computer-readable storage medium may be any available medium that a computer can access or a data storage device such as a server, a data center, or the like that includes one or more available media integration. The available medium may be a magnetic medium (e.g., floppy disk, hard disk, magnetic tape), an optical medium (e.g., DVD), or semiconductor medium (e.g., Solid State Disk (SSD)) or the like It can be seen from the above technical solutions that, according to the electronic device for predicting the Vault after phakic intraocular lens in the embodiment of the present invention, the collected related data are directly obtained by the human-computer interaction module, and then direct calculation is carried out according to the data, so that the Vault after operation is quantitatively predicted, and meanwhile, expected predicting accuracy and precision are realized, an operation precision is significantly improved, and an operation risk is reduced. Meanwhile, the use is simple and follows procedures, without needing complicated operations, which facilitates a refractive surgeon to simply improve a clinical effect of ICL lens implantation according to relevant standardized operation procedures on the premise of ensuring safety.

The above descriptions are only descriptions of the preferred embodiments of the present invention and the applied technical principles, and are not intended to limit the scope of the present invention sought to be protected, but only represent the preferred embodiments of the present invention. Those skilled in the art should understand that the scope of invention involved in the present invention is not limited to the technical solution formed by the specific combination of the above technical features, but also covers other technical solutions formed by any combination of the above technical features or their equivalent features without departing from the inventive concept. Based on the embodiments of the present invention, all other embodiments obtained by those skilled in the art without going through any creative work should fall within the scope of protection of the present invention.

The invention claimed is:

1. A method for predicting a Vault after phakic intraocular lens, comprising the following steps of:

step S1: obtaining a thickness (LT) of a to-be-corrected crystalline lens;

step S2: obtaining a horizontal sulcus-to-sulcus (STSH) value and a vertical sulcus-to-sulcus (STSV) value corresponding to the to-be-corrected crystalline lens; wherein the STSH value and the STSV value are obtained through examination images using an ultrasound biomicroscope (UBM) or a biometer; wherein examination images with blurry boundaries are excluded;

step S3: collecting a size of a preset implantable collamer (ICL) lens, comprising a diameter ICL Size and an axial position ICL Ax of the ICL lens;

step S4: calculating an effective sulcus-to-sulcus (STS) value at the axial position of the ICL lens by formulas (1) and (2) according to the STSH value and the STSV value:

when ICL Ax≤90, $$STS=STSH-(STSH-STSV)\times\sin ICL\ Ax\times 1586.5 \div 1555 \quad (1);$$

and
when ICL Ax>90, $$STS=STSH-(STSH-STSV)\times\sin(180-ICL\ Ax)\times 1586.5 \div 1555 \quad (2);$$

step S5: calculating a lens thickness influence factor (LTF) by formula (3) according to the LT:

$$LTF=LT \div 10+0.16 \quad (3);$$

step S6: calculating a Vault chord height (h) by formula (4) according to the ICL Size and the STS:

$$h=(ICL\ Size-STS)^{0.7} \quad (4);$$

step S7: calculating the Vault by formula (5) according to the h and the LTF:

$$Vault=h-LTF \quad (5);$$

and step S8: judging whether the Vault reaches a threshold:

if the Vault does not reach the threshold, updating the diameter ICL Size and the axial position ICL Ax of the ICL lens, and entering the step S4; wherein the updating of the diameter ICL Size and the axial position ICL Ax of the ICL lens is changed and selected based on the size of the present ICL lens according to a difference between the Vault and the threshold; and if the Vault reaches the threshold, outputting the diameter ICL size and the axial position ICL Ax and implanting and placing the ICL lens with the ICL size at the axial position ICL Ax.

2. The method for predicting the Vault after phakic intraocular lens according to claim 1, wherein the size of the preset ICL lens is selected according to at least one of experience and STSH, STSV and LT data.

3. The method for predicting the Vault after phakic intraocular lens according to claim 1, wherein the threshold is a point value or a range.

4. The method for predicting the Vault after phakic intraocular lens according to claim 3, wherein the threshold ranges from 0.5 to 1.0; and when the Vault falls within the range of the threshold, the Vault reaches the threshold.

5. A method for determining a lens size of phakic intraocular lens, comprising:

step S1: obtaining a thickness (LT) of a to-be-corrected crystalline lens;

step S2: obtaining a horizontal sulcus-to-sulcus (STSH) value and a vertical sulcus-to-sulcus (STSV) value corresponding to the to-be-corrected crystalline lens; wherein the STSH value and the STSV value are obtained through examination images using an ultrasound biomicroscope (UBM) or a biometer; wherein examination images with blurry boundaries are excluded;

step S3: collecting a size of a preset ICL lens, comprising a diameter ICL Size and an axial position ICL Ax of the ICL lens;

step S4: calculating an effective sulcus-to-sulcus (STS) value at the axial position of the ICL lens by formulas (1) and (2) according to the STSH value and the STSV value:

when ICL Ax≤90, $$STS=STSH-(STSH-STSV)\times\sin ICL\ Ax\times 1586.5 \div 1555 \quad (1);$$

and
when ICL Ax>90, $$STS=STSH-(STSH-STSV)\times\sin(180-ICL\ Ax)\times 1586.5 \div 1555 \quad (2);$$

step S5: calculating a lens thickness influence factor (LTF) by formula (3) according to the LT:

$$LTF=LT \div 10+0.16 \quad (3);$$

step S6: calculating a Vault chord height (h) by formula (4) according to the ICL Size and the STS:

$$h=(ICL\ Size-STS)^{0.7} \quad (4);$$

step S7: calculating the Vault by formula (5) according to the h and the LTF:

$$Vault=h-LTF \quad (5);$$

and step S8: judging whether the Vault reaches a threshold:

if the Vault does not reach the threshold, updating the diameter ICL Size and the axial position ICL Ax of the ICL lens, and entering the step S4; wherein the updating of the diameter ICL Size and the axial position ICL Ax of the ICL lens is changed and selected based on the size of the present ICL lens according to a difference between the Vault and the threshold; and if the Vault reaches the threshold, outputting the diameter ICL size and the axial position ICL Ax and implanting and placing the ICL lens with the ICL size at the axial position ICL Ax.

6. An electronic device, comprising a processor, a memory and a human-computer interaction module; and data transmission being carried out among the processor, the memory and the human-computer interaction module, wherein:

the human-computer interaction module is configured for inputting collected data and sending the collected data to the processor;

the memory is configured for storing a computer program and related data; and the processor is configured for receiving the data input by the human-computer interaction module, and executing the program stored in the memory; and when receiving the data input by the human-computer interaction module, implementing the following steps of:

step S1: obtaining a thickness (LT) of a to-be-corrected crystalline lens;

step S2: obtaining a horizontal sulcus-to-sulcus (STSH) value and a vertical sulcus-to-sulcus (STSV) value corresponding to the to-be-corrected crystalline lens; wherein the STSH value and the STSV value are obtained through examination images using an ultrasound biomicroscope (UBM) or a biometer; wherein examination images with blurry boundaries are excluded;

step S3: collecting a size of a preset ICL lens, comprising a diameter ICL Size and an axial position ICL Ax of the ICL lens;

when executing the program stored in the memory, implementing the following steps of:

step S4: calculating an effective sulcus-to-sulcus (STS) value at the axial position of the (ICL) lens by formulas (1) and (2) according to the STSH value and the STSV value:

when ICL Ax≤90, $$STS=STSH-(STSH-STSV)\times \sin ICL\ Ax\times 1586.5\div 1555 \quad (1);$$

and
when ICL Ax>90, $$STS=STSH-(STSH-STSV)\times \sin(180-ICL\ Ax)\times 1586.5\div 1555 \quad (2);$$

wherein in the step, formula parameters are determined through a lot of experiments and theoretical derivation;

step S5: calculating a lens thickness influence factor (LTF) by formula (3) according to the LT:

$$LTF=LT\div 10+0.16 \quad (3);$$

step S6: calculating a Vault chord height (h) by formula (4) according to the ICL Size and the STS:

$$h=(ICL\ Size-STS)^{0.7} \quad (4);$$

step S7: calculating the Vault by formula (5) according to the h and the LTF:

$$Vault=h-LTF \quad (5);$$

and
step S8: judging whether the Vault reaches a threshold:
if the Vault does not reach the threshold, updating the diameter ICL Size and the axial position ICL Ax of the ICL lens, and entering the step S4; wherein the updating of the diameter ICL Size and the axial position ICL Ax of the ICL lens is changed and selected based on the size of the present ICL lens according to a difference between the Vault and the threshold; and if the Vault reaches the threshold, outputting the diameter ICL size and the axial position ICL Ax and implanting and placing the ICL lens with the ICL size at the axial position ICL Ax.

* * * * *